(12) United States Patent
Sohn

(10) Patent No.: US 11,071,757 B2
(45) Date of Patent: Jul. 27, 2021

(54) **COMPOSITION FOR PREVENTING OR TREATING INFLAMMATORY DISEASE COMPRISING THE VENOM OF *AGKISTRODON PISCIVORUS PISCIVORUS* OR *NAJA MELANOLEUCA***

(71) Applicant: DNBIO PHARM, INC., Changwon-si (KR)

(72) Inventor: Seonghyang Sohn, Suwon-si (KR)

(73) Assignee: DNBIO Pharm, Inc., Changwon-si (KR)

( * ) Notice: Subject to any disclaimer, the term of this patent is extended or adjusted under 35 U.S.C. 154(b) by 0 days.

(21) Appl. No.: 16/430,957

(22) Filed: Jun. 4, 2019

(65) Prior Publication Data
US 2019/0282626 A1 Sep. 19, 2019

Related U.S. Application Data

(63) Continuation of application No. PCT/KR2017/014391, filed on Dec. 8, 2017.

(30) Foreign Application Priority Data

Dec. 9, 2016 (KR) .......................... 10-2016-0167867
Dec. 9, 2016 (KR) .......................... 10-2016-0167868

(51) Int. Cl.
| | | |
|---|---|---|
| *A61K 35/583* | (2015.01) | |
| *A61P 17/02* | (2006.01) | |
| *A61K 9/00* | (2006.01) | |
| *A61Q 19/00* | (2006.01) | |
| *A61K 8/98* | (2006.01) | |

(52) U.S. Cl.
CPC .............. *A61K 35/583* (2013.01); *A61K 8/98* (2013.01); *A61K 9/0014* (2013.01); *A61P 17/02* (2018.01); *A61Q 19/00* (2013.01)

(58) Field of Classification Search
None
See application file for complete search history.

(56) References Cited

U.S. PATENT DOCUMENTS

| 4,341,762 A | 7/1982 | Haast | |
|---|---|---|---|
| 2009/0209468 A1* | 8/2009 | Reid | ................ A61K 38/1703 |
| | | | 514/17.7 |

FOREIGN PATENT DOCUMENTS

| CN | 102526114 A | 7/2012 | |
|---|---|---|---|
| KR | 10-1802514 B1 | 11/2017 | |
| KR | 10-1802515 B1 | 11/2017 | |
| WO | 2006/018844 A1 | 2/2006 | |
| WO | WO-2006018844 A1 * | 2/2006 | ................ A61P 1/16 |

OTHER PUBLICATIONS

International Search Report of PCT/KR2017/014391 dated Mar. 15, 2018 [PCT/ISA/210].

* cited by examiner

*Primary Examiner* — Russell G Fiebig
(74) *Attorney, Agent, or Firm* — Sughrue Mion, PLLC

(57) ABSTRACT

A pharmaceutical composition for preventing or treating inflammatory disease comprising snake venom is disclosed. More specifically, the pharmaceutical composition or quasi-drug includes venom of *Agkistrodon piscivorus piscivorus* or *Naja melanoleuca* as an active ingredient. A method for preventing or treating inflammatory disease includes administering the venom of *Agkistrodon piscivorus piscivorus* or *Naja melanoleuca* to a subject. The composition can increase the expression of C-C chemokine receptor type 1 (CCR1) in a mouse where skin ulcer is induced and thus has an excellent effect of treating skin ulcers, and thus can be effectively used for the treatment of skin ulcers, in particular Behcet's disease or Buerger's disease.

6 Claims, 1 Drawing Sheet
(1 of 1 Drawing Sheet(s) Filed in Color)

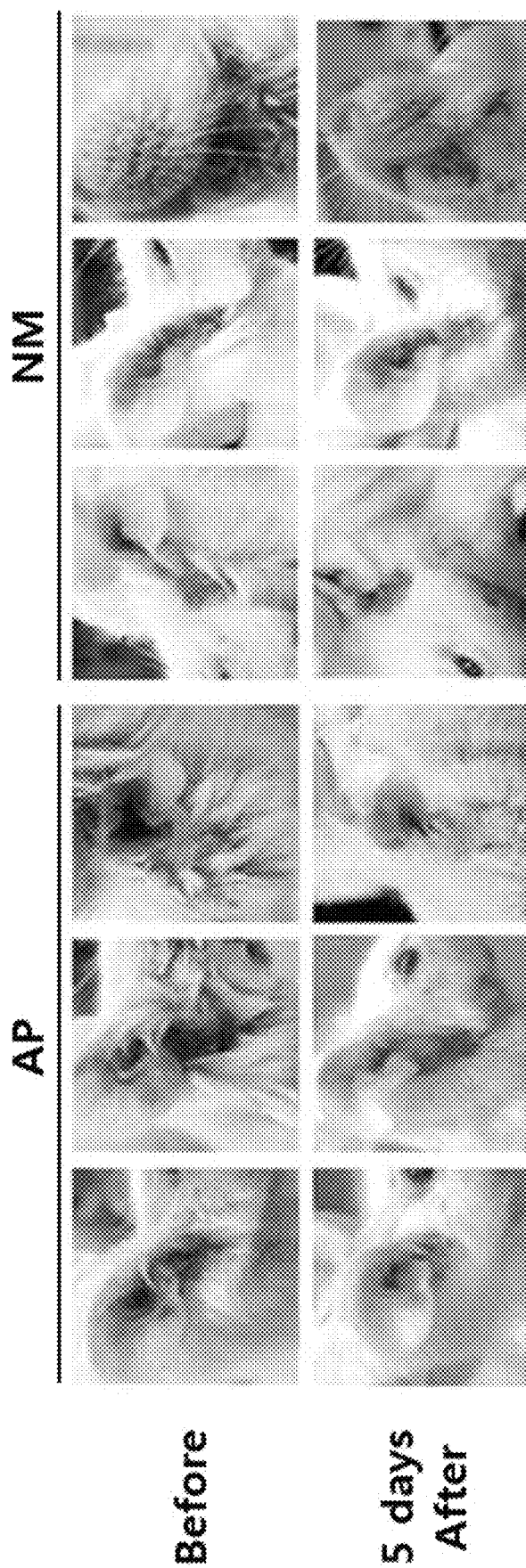

COMPOSITION FOR PREVENTING OR TREATING INFLAMMATORY DISEASE COMPRISING THE VENOM OF *AGKISTRODON PISCIVORUS PISCIVORUS* OR *NAJA MELANOLEUCA*

CROSS REFERENCE TO RELATED APPLICATIONS

This application is a Continuation-In-Part of International Application No. PCT/KR2017/014391, filed Dec. 8, 2017, claiming priorities to Korean Patent Application Nos. 10-2016-0167867 and 10-2016-0167868, filed Dec. 9, 2016 respectively.

BACKGROUND OF THE INVENTION

Field of the Invention

The present invention relates to a composition for preventing or treating inflammatory disease comprising snake venom, and more specifically, to a pharmaceutical composition or quasi-drug composition for preventing or treating inflammatory disease comprising the venom of *Agkistrodon piscivorus piscivorus* or *Naja melanoleuca* as an active ingredient, and a method for preventing or treating inflammatory disease which includes administering the composition to a subject or applying the composition to a subject to the skin.

The composition for preventing or treating inflammatory disease comprising snake venom of the present invention can increase the expression of C-C chemokine receptor type 1 (CCR1) in a mouse where skin ulcer is induced, and thus has an excellent effect of treating skin ulcers. Therefore, the composition can be effectively used by applying to pharmaceutical drugs, etc. including skin external agents for the treatment of skin ulcers, in particular for the treatment of Behcet's disease or Buerger's disease.

Related Art

Behcet's disease is a rare intractable inflammatory disease in which the symptoms include recurrent aphthous ulcers of the mouth and/or genitalia, uveitis, and skin lesions. Clinical symptoms of Behcet's disease include not only skin ulcers but also severe chronic inflammation in joints, central nervous system, intestine, kidneys, urogenital system, cardiovascular, accompanied by digestive system related symptoms (e.g., enterohemorrhage, enterobrosia), superior and inferior vena cava syndrome, aortic regurgitation, etc. manifests in multiple dimensions. These symptoms are associated with systemic vasculitis, which is a central pathophysiological characteristic of Behcet's disease. The exact cause of Behcet's disease remains unclear, but autoimmunity and autoinflammation are major causes.

In Behcet's disease, macrophages, dendritic cells, $CD4^+$ and $CD8^+$ T cells, and neutrophils are involved in cell invasion. Additionally, the Behcet's disease is also associated with an increase in cytokine production.

In patients with Behcet's disease, the results with regard to gene variations of interleukin-10 (IL-10) (i.e. cytokine) and C-C chemokine receptor type 1 (CCR1) are already reported. IL-10 and GM-CSF function as CCR1 activators, and the expression level of IL-10 protein is low in the serum of Behcet's disease patients. Therefore, expression level of CCR1 can increase using IL10, CCR1 activator. However, even if the function of IL-10 as a therapeutic agent is confirmed, there is still a disadvantage in that the manufacturing-related costs or storage-related costs (e.g., refrigeration storage, etc.) are expensive.

SUMMARY OF THE INVENTION

In this regard, the present inventors have made efforts to develop a method for solving the conventional problems of therapeutic agents for Behcet's disease and for the fundamental treatment of inflammatory disease including Behcet's disease. As a result, we have invented a composition for preventing or treating inflammatory disease comprising the venom of *Agkistrodon piscivorus piscivorus* or *Naja melanoleuca* as an active ingredient.

Another object of the present invention is to provide a pharmaceutical composition for preventing or treating inflammatory disease comprising the venom of *Agkistrodon piscivorus piscivorus* or *Naja melanoleuca* as an active ingredient.

An object of the present invention is to provide a quasi-drug for preventing or treating inflammatory disease containing the venom of *Agkistrodon piscivorus piscivorus* or *Naja melanoleuca* as an active ingredient.

Still another object of the present invention is to provide a method for preventing or treating inflammatory disease, which includes administering the venom of *Agkistrodon piscivorus piscivorus* or *Naja melanoleuca* to a subject.

Still another object of the present invention is to provide a method for treating inflammatory disease, which includes applying the venom of *Agkistrodon piscivorus piscivorus* or *Naja melanoleuca* to the skin of a subject.

It was confirmed that the composition comprising the venom of *Agkistrodon piscivorus piscivorus* or *Naja melanoleuca* according to the present invention as an active ingredient can increase the expression of C-C chemokine receptor type 1 (CCR1) in a mouse where skin ulcer is induced.

Accordingly, the composition has an excellent treatment effect for skin ulcers and thus the composition is expected to be effectively used by applying to pharmaceutical drugs, etc. including skin external agents for the treatment of skin ulcers, in particular for the treatment of Behcet's disease or Buerger's disease.

The present invention provides not only a composition for preventing or treating inflammatory disease comprising the venom of *Agkistrodon piscivorus piscivorus* or *Naja melanoleuca* as an active ingredient, but also a method for treating inflammatory disease using the composition.

As used herein, the term "Behcet's disease" is a rare intractable inflammatory disease, and it is divided into a symptomatic Behcet's disease (when there is a symptom) and a asymptomatic Behcet's disease (when there is no symptom).

According to a first embodiment, the present invention provides a pharmaceutical composition for preventing or treating inflammatory disease containing the venom of *Agkistrodon piscivorus piscivorus* or *Naja melanoleuca* as an active ingredient.

The venom of *Agkistrodon piscivorus piscivorus* or *Naja melanoleuca* can increase the expression of C-C chemokine receptor type 1 (CCR1).

The inflammatory disease may include skin ulcers. Additionally, the inflammatory disease may be Behcet's disease or Buerger's disease.

The inflammatory disease may include skin ulcers induced from Behcet's disease or Buerger's disease.

The pharmaceutical composition according to the present invention may be used after formulating into various forms according to each conventional method. For example, the pharmaceutical composition may be formulated into oral formulations (e.g., powders, granules, tablets, capsules, suspensions, emulsions, syrups, etc.), and may be used after formulating in the form of external agents, suppositories, and sterile injection solutions. However, it is most preferred that the composition of the present invention be provided in the form of a skin external agent for the purpose of treating inflammatory disease. Specifically, the composition of the present invention may be used in the form of a skin external agent (e.g., liquids, ointments, creams, lotions, sprays, patches, gels, aerosols, etc.).

According to the formulation, the pharmaceutical composition may be prepared by further containing a pharmaceutically acceptable carrier, for example, a carrier known in the art such as a buffer, preservative, analgesic, solubilizer, isotonic agent, stabilizer, base, excipient, lubricant, etc. For example, in the case of a skin external agent used locally at the ulcer, for example, a preservative, a solvent to aid drug penetration, and an emollient, etc. in the case of ointments and creams, and a conventional carrier such as ethanol and oleyl alcohol may be contained.

The pharmaceutical composition may further contain a compound commonly used in the treatment of inflammatory disease (e.g., antibiotics, antiinflammatory agents, preparations for skin treatment, anesthetics, analgesics, etc). These may be appropriately modified according to the respective formulation, and may be preferably contained when the composition is provided in the form of a skin external agent, but are not limited thereto.

The pharmaceutical composition may be administered in a pharmaceutically effective amount. As used herein, the term "pharmaceutically effective amount" refers to an amount sufficient for the treatment of diseases at a reasonable benefit/risk ratio applicable to medical treatment without causing any side effects, and the level of the effective dose may be determined based on the factors including health state of the patient, type of ulcer, severity of illness, drug activity, sensitivity to drug, administration method, administration time, administration route and dissolution rate, length of treatment, drug to be used in combination or simultaneously, and other factors well known in the medical field. The composition of the present invention may be administered as an individual therapeutic agent, in combination with another therapeutic agent, or sequentially or simultaneously with a conventional therapeutic agent, and may be administered once or multiple times.

According to a second embodiment, the present invention provides a quasi-drug for treating inflammatory disease comprising the venom of *Agkistrodon piscivorus piscivorus* or *Naja melanoleuca* as an active ingredient.

As used herein, the term "quasi-drug" refers to a product which falls under any of the followings: fiber- or rubber products or analogs thereof which are used for the cure, alleviation, treatment, or prevention of disease in humans or animals; products other than instruments and machines, and analogs thereof which have a weak action in humans or do not directly act upon the human body; and products corresponding to any of the germicides or insecticides, and analogs thereof for the prevention of infections. In addition, the quasi-drug refers to a product, which excludes those other than instruments, machines, and apparatus among the products which are used for the diagnosis, cure, alleviation, treatment, or prevention of disease in humans or animals; or excludes those other than instruments, machines, and apparatus among the products which are used for providing pharmacological effects on the structures and functions of humans or animals.

When the venom of *Agkistrodon piscivorus piscivorus* or *Naja melanoleuca* according to the present invention is used as a quasi-drug, the composition may be directly added as it is or may be used along with other quasi-drugs or components of other quasi-drugs, and may be appropriately used according to conventional methods. In particular, the amount of the active ingredient to be mixed may be appropriately determined depending on the purpose of use.

It is preferred that the quasi-drug of the present invention be a disinfect cleaner, shower foam, oral cleanser (garglin), water wipe, detergent soap, hand wash, humidifier filler, mask, ointment, or filter filler, but it is not limited thereto.

According to a third embodiment, the present invention provides a method for preventing or treating inflammatory disease which includes administering the venom of *Agkistrodon piscivorus piscivorus* or *Naja melanoleuca* to a subject. The venom of *Agkistrodon piscivorus piscivorus* or *Naja melanoleuca* is as described above and the effect of the venom for inflammatory disease is also as described above.

As used herein, the term "subject" refers to all animals which include mammals (e.g. including mice, livestock, humans, etc.).

The venom of *Agkistrodon piscivorus piscivorus* or *Naja melanoleuca* of the present invention may be used to treat inflammatory disease or to promote the treatment of inflammatory disease by administering it to a subject. Specifically, when the venom of *Agkistrodon piscivorus piscivorus* or *Naja melanoleuca* is provided in the form of a skin external agent, it may be applied to the skin of a subject to treat inflammatory disease. Additionally, the venom of *Agkistrodon piscivorus piscivorus* or *Naja melanoleuca* can be used for the treatment of disease related to inflammatory disease or various diseases resulting from inflammatory disease as well as for the treatment of inflammatory disease.

According to a fourth embodiment, the present invention provides a method for preventing or treating inflammatory disease which includes applying the venom of *Agkistrodon piscivorus piscivorus* or *Naja melanoleuca* to a subject.

The venom of *Agkistrodon piscivorus piscivorus* or *Naja melanoleuca* of the present invention does not cause any side effect even when it is used as a pharmaceutical composition, etc. and thus can be used safely.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows images confirming the states of skin ulcer in mice with symptomatic Behcet's disease 5 days after administrating of the venom of *Agkistrodon piscivorus piscivorus* or *Naja melanoleuca* of the present invention to the mice.

DESCRIPTION OF EXEMPLARY EMBODIMENTS

Hereinafter, the present invention will be described in detail with reference to the following examples. However, the following examples are illustrative of the present invention, and the contents of the present invention are not limited by the following examples

EXAMPLES

Example 1. Preparation of Mice

Four-week-old ICR strain mice were used. Normal mice were subjected to hair cut before skin application, and then, a solution containing the venom of *Agkistrodon piscivorus piscivorus* or *Naja melanoleuca* was applied to the mice using cotton swabs. In the case of oral administration, the same amount was orally administered. For the mice with Behcet's disease, the venom of *Agkistrodon piscivorus piscivorus* or *Naja melanoleuca* was applied to the regions with skin symptoms (e.g. ulcers, erythema, etc.) using cotton swabs.

Example 2. Flow Cytometry

After isolating the peripheral blood cells of each mouse, the red blood cells were removed and fluorescence-labeled anti-CCR1 antibody was reacted with cells and the results were analyzed by a flow cytometer and thereby the frequency of cells expressing CCR1 in each mouse was measured. Cells were isolated from the lymph node of each mouse and then reacted with the antibody in the same manner and analyzed.

Experimental Example

Experimental Example 1. Confirmation of Characteristics of CCR1 Expression in Mice with Behcet's Disease To confirm the characteristics of CCR1 expression in mice with Behcet's disease, PBMCs (peripheral blood mononuclear cells) and lymph nodes were isolated for each of normal mice (control group), mice with symptomatic Behcet's disease, and mice with asymptomatic Behcet's disease, and the CCR1 expression in each group was analyzed by flow cytometry. The results are shown in Table 1 below.

As shown in Table 1 above, it was confirmed that the CCR1 expression was lower in the mice with symptomatic Behcet's disease (PBMC: surface 7.92±2.73%, cytoplasm 30.37±19.47%, and Lymph Node: surface 8.94±2.43%, cytoplasm 64.90±17.62%), compared to those in the mice of the control group (PBMC: surface 8.35±1.32%, cytoplasm 65.61±14.15%, and Lymph Node: surface 10.15±4.18%, cytoplasm 50.26±11.52%) and the mice with asymptomatic Behcet's disease (PBMC: surface 11.92±3.09%, cytoplasm 64.34±4.60%, and Lymph Node: surface 10.75±2.59%, cytoplasm 72.7±26.88%). Accordingly, contrary to those in the mice where Behcet's disease has not occurred and the mice where asymptomatic Behcet's disease has occurred, the CCR1 expression was shown to be significantly lower in the PBMCs and lymph nodes of the mice with symptomatic Behcet's disease.

Experimental Example 2. Confirmation of Characteristics of CCR1 Expression in Normal Mice by the Venom of *Naja melanoleuca*

To confirm the effects of the venom of *Naja melanoleuca* (NM) on CCR1 expression in normal mice, the venom of *Naja melanoleuca* was applied to each of the skin of normal mice (local administration) and oral cavity (oral administration), and the PBMCs and lymph nodes were isolated and the CCR1 expression therein was analyzed by flow cytometry. The results are shown in Table 2 below.

TABLE 1

|  | Normal Control | | | | BD | | | | BDN | | | |
|---|---|---|---|---|---|---|---|---|---|---|---|---|
|  | Surface | | Cytoplasm | | Surface | | Cytoplasm | | Surface | | Cytoplasm | |
|  | PBMC | Lymph Node | PBMC | Lymph Node | PBMC | Lymph Node | PBMC | Lymph Node | PBMC | Lymph Node | PBMC | Lymph Node |
|  | 8.4 | 8.7 | 50.1 | 42.2 | 10.3 | 5.8 | 18.2 | 84.7 | 12.6 | 8.5 | 71 | 98.8 |
|  | 5.8 | 4.0 | 49.6 | 31.2 | 11.3 | 11.8 | 34.9 | 85.5 | 13.2 | 8.6 | 67.2 | 97.9 |
|  | 8.5 | 10.6 | 64.6 | 59.2 | 9 | 9.8 | 62.1 | 85.4 | 16.1 | 8.1 | 69.7 | 98.9 |
|  | 9.6 | 8.7 | 69 | 61.8 | 6 | 6.9 | 49.2 | 72.5 | 9.6 | 10.8 | 62.6 | 92.3 |
|  | 8.8 | 16.5 | 74.4 | 54.3 | 8.7 | 11.5 | 11.1 | 43.1 | 7.1 | 14.9 | 62 | 48.7 |
|  | 9.0 | 12.4 | 86.0 | 52.9 | 4 | 8.5 | 23.8 | 58 | 11.9 | 11.5 | 59.6 | 41.8 |
|  |  |  |  |  | 6.2 | 8.3 | 13.3 | 25.1 | 13 | 12.9 | 58.3 | 30.7 |
| Avg | 8.35 | 10.15 | 65.61 | 50.26 | 7.92 | 8.94 | 30.37 | 64.9 | 11.92 | 10.75 | 64.34 | 72.7 |
| SD | 1.32 | 4.18 | 14.15 | 11.52 | 2.73 | 2.43 | 19.47 | 17.62 | 3.09 | 2.59 | 4.60 | 26.88 |
| p value | 0.01 |  |  |  |  |  |  |  | 0.01 |  |  |  |
|  |  |  |  |  | 0.018 |  |  |  | 0.018 |  |  |  |
|  |  |  |  |  |  |  | 0.0007 |  |  |  | 0.0007 |  |
|  |  |  | 0.003 |  |  |  | 0.003 |  |  |  |  |  |

TABLE 2

| | Normal Control | | | | NM Skin | | | | NM Oral | | | |
|---|---|---|---|---|---|---|---|---|---|---|---|---|
| | Surface | | Cytoplasm | | Surface | | Cytoplasm | | Surface | | Cytoplasm | |
| | PBMC | Lymph Node | PBMC | Lymph Node | PBMC | Lymph Node | PBMC | Lymph Node | PBMC | Lymph Node | PBMC | Lymph Node |
| | 8.4 | 8.7 | 50.1 | 42.2 | 6.2 | 12.0 | 72.7 | 44 | 12.3 | 10.0 | 54.9 | 33.3 |
| | 5.8 | 4.0 | 49.6 | 31.2 | 7.8 | 11.2 | 59.6 | 48.7 | 1.2 | 7.4 | 47.8 | 87.4 |
| | 8.5 | 10.6 | 64.6 | 59.2 | 9.1 | 10.7 | 90.5 | 66.3 | 10.8 | 8.5 | 72.9 | 47.0 |
| | 9.6 | 8.7 | 69 | 61.8 | 7.9 | 10.4 | 75.6 | 58.2 | 11.2 | 8.4 | 75.3 | 59.6 |
| | 8.8 | 16.5 | 74.4 | 54.3 | 12.6 | 13.4 | 64.5 | 58.0 | 20 | 13.4 | 49.9 | 61.6 |
| | 9.0 | 12.4 | 86.0 | 52.9 | 5.4 | 13.5 | 62.7 | 64.8 | 14.9 | 16.3 | 70.1 | 74.2 |
| Avg | 8.35 | 10.15 | 65.61 | 50.26 | 8.16 | 11.86 | 70.96 | 56.66 | 11.73 | 10.66 | 61.81 | 60.5 |
| SD | 1.32 | 4.18 | 14.15 | 11.52 | 2.53 | 1.34 | 11.36 | 8.79 | 6.17 | 3.46 | 12.3 | 19.14 |

As shown in Table 2 above, it was confirmed that the CCR1 expression was slightly increased in the mice where the venom of *Naja melanoleuca* was applied to the skin of normal mice (PBMC: surface 8.16±2.53%, cytoplasm 70.93±11.36%, and Lymph Node: surface 11.86±1.34%, cytoplasm 56.66±8.79%) and in the mice where the venom of *Naja melanoleuca* was administered to oral cavity of normal mice (PBMC: surface 11.73±6.17%, cytoplasm 61.81±12.3%, and Lymph Node: surface 10.66±3.46%, cytoplasm 60.5±19.14%), compared to the CCR1 expression in normal mice without any treatment (PBMC: surface 8.35±1.32%, cytoplasm 65.61±14.15%, and Lymph Node: surface 10.15±4.18%, cytoplasm 50.26±11.52%).

Experimental Example 3. Confirmation of Characteristics of CCR1 Expression in Normal Mice by the Venom of *Agkistrodon piscivorus piscivorus*

To confirm the effects of the venom of *Agkistrodon piscivorus piscivorus* on CCR1 expression in normal mice, the venom of *Agkistrodon piscivorus piscivorus* was applied to each of the skin of normal mice (local administration) and oral cavity (oral administration), and the PBMCs and lymph nodes were isolated and the CCR1 expression therein was analyzed by flow cytometry. The results are shown in Table 3 below.

14.75±3.67%, cytoplasm 50.6±18.50%) and in the mice where the venom of *Agkistrodon piscivorus piscivorus* was administered to oral cavity of normal mice (PBMC: surface 10.2±3.98%, cytoplasm 49.18±14.27%, and Lymph Node: surface 17.51±4.74%, cytoplasm 63.98±15.44%), compared to the CCR1 expression in normal mice without any treatment (PBMC: surface 8.35±1.43%, cytoplasm 65.61±14.15%, and Lymph Node: surface 10.15±4.18%, cytoplasm 50.26±11.52%).

Experimental Example 4. Confirmation of Effects of the Venom of *Agkistrodon piscivorus piscivorus* (AP) or *Naja melanoleuca* (NM) on CCR1 Expression in Mice with Symptomatic Behcet's Disease To confirm the effects of the venom of *Agkistrodon piscivorus piscivorus* (AP) or *Naja melanoleuca* (NM) on CCR1 expression in mice with symptomatic Behcet's disease, the venom of *Agkistrodon piscivorus piscivorus* was applied to the skin of mice with symptomatic Behcet's disease (local administration), and the PBMCs and lymph nodes were isolated and the CCR1 expression therein was

TABLE 3

| | Normal Control | | | | AP Skin | | | | AP Oral | | | |
|---|---|---|---|---|---|---|---|---|---|---|---|---|
| | Surface | | Cytoplasm | | Surface | | Cytoplasm | | Surface | | Cytoplasm | |
| | PBMC | Lymph Node | PBMC | Lymph Node | PBMC | Lymph Node | PBMC | Lymph Node | PBMC | Lymph Node | PBMC | Lymph Node |
| | 8.4 | 8.7 | 50.1 | 42.2 | 6.1 | 10.7 | 38.2 | 30 | 17.5 | 12.5 | 31.2 | 38.6 |
| | 5.8 | 4.0 | 49.6 | 31.2 | 7 | 16.7 | 42.2 | 30.4 | 11.1 | 12.3 | 36.2 | 52.6 |
| | 8.5 | 10.6 | 64.6 | 59.2 | 7 | 18.6 | 66.7 | 57.1 | 6.7 | 15.3 | 66.5 | 79.7 |
| | 9.6 | 8.7 | 69 | 61.8 | 6 | 9.3 | 65.4 | 56.8 | 7.8 | 22.2 | 62.5 | 67 |
| | 8.8 | 16.5 | 74.4 | 54.3 | 14.4 | 16.6 | 71.5 | 67.6 | 7.5 | 20.1 | 54.3 | 72.9 |
| | 9.0 | 12.4 | 86.0 | 52.9 | 12.8 | 16.6 | 65.4 | 73.7 | 10.6 | 22.7 | 44.4 | 73.1 |
| Avg | 8.35 | 10.15 | 65.61 | 50.26 | 8.88 | 14.75 | 58.23 | 52.6 | 10.2 | 17.51 | 49.18 | 63.98 |
| SD | 1.32 | 4.18 | 14.15 | 11.52 | 3.71 | 3.78 | 14.20 | 18.50 | 3.98 | 4.74 | 14.27 | 15.44 |
| p value | | 0.07 | | | | 0.07 | | | | 0.017 | | |
| | | 0.017 | | | | | | | | | | |

As shown in Table 3 above, it was confirmed that the CCR1 expression was slightly increased in the mice where the venom of *Agkistrodon piscivorus piscivorus* was applied to the skin of normal mice (PBMC: surface 8.88±3.71%, cytoplasm 58.23±14.20%, and Lymph Node: surface analyzed by flow cytometry. The results are shown in Table 4 below. Additionally, the venom of *Agkistrodon piscivorus piscivorus* was administered to mice with symptomatic Behcet's disease, and 5 days thereafter, the resulting changes in skin ulcer of the mice are shown in FIG. 1.

TABLE 4

| | BD | | | | BD + AP | | | | BD + NM | | | |
|---|---|---|---|---|---|---|---|---|---|---|---|---|
| | Surface | | Cytoplasm | | Surface | | Cytoplasm | | Surface | | Cytoplasm | |
| | PBMC | Lymph Node | PBMC | Lymph Node | PBMC | Lymph Node | PBMC | Lymph Node | PBMC | Lymph Node | PBMC | Lymph Node |
| | 10.3 | 5.8 | 18.2 | 84.7 | 14.2 | 18.7 | 54.9 | 20.4 | 9.3 | 16.5 | 67.8 | 47.9 |
| | 11.3 | 11.8 | 34.9 | 85.5 | 13.2 | 17.6 | 42.9 | 15.2 | 16.7 | 13.5 | 79.7 | 46.1 |
| | 9 | 9.8 | 62.1 | 85.4 | 4.7 | 23.1 | 71.6 | 33.4 | 17.8 | 15.3 | 79.8 | 39.7 |
| | 6 | 6.9 | 49.2 | 72.5 | 19.9 | 21.4 | 61.1 | 37 | 18.9 | 27.6 | 89.8 | 70.4 |
| | 8.7 | 11.5 | 11.1 | 43.1 | 25.1 | 26.7 | 48.5 | 69.3 | 18.3 | 28.8 | 85.4 | 62.9 |
| | 4 | 8.5 | 23.8 | 58 | 24.1 | 34.4 | 59.9 | 51.1 | 23.6 | 31.2 | 67.7 | 53.4 |
| | 6.2 | 8.3 | 13.3 | 25.1 | 23.8 | 32.6 | 65.4 | 52.7 | 27.6 | 23.3 | 79.5 | 50.7 |
| | | | | | 27.2 | 29.5 | 63.8 | 28.9 | | | | |
| Avg | 7.92 | 8.94 | 30.37 | 64.9 | 19.02 | 25.5 | 58.51 | 38.5 | 18.88 | 22.31 | 78.52 | 53.01 |
| SD | 2.73 | 2.43 | 19.47 | 17.62 | 7.70 | 6.30 | 9.35 | 18.12 | 5.72 | 7.19 | 8.27 | 10.46 |
| p value | 0.003 | | | | 0.003 | | | | | | | |
| | 0.0006 | | | | | | | | 0.0006 | | | |
| | | 0.00002 | | | | 0.00002 | | | | | | |
| | | 0.0005 | | | | | | | | 0.0005 | | |
| | | | 0.003 | | | | 0.003 | | | | | |
| | | | 0.00006 | | | | | | | | 0.00006 | |
| | | | | | | | | 0.0008 | | | | 0.0008 |
| | | | | 0.03 | | | | 0.03 | | | | |

As shown in Table 4 above, it was confirmed that the CCR1 expression was significantly increased in the group of mice with symptomatic Behcet's disease where the venom of *Agkistrodon piscivorus piscivorus* was administered (PBMC: surface 19.02±7.70%, cytoplasm 58.51±9.35%, and Lymph Node: surface 25.5±6.30%, cytoplasm 38.5±18.12%) or in the group of mice with symptomatic Behcet's disease where the venom of *Naja melanoleuca* was administered (PBMC: surface 18.88±5.72%, cytoplasm 78.52±8.27%, and Lymph Node: surface 22.31±7.19%, cytoplasm 53.01±10.46%), respectively, compared to the group where none of the venom was administered (PBMC: surface 7.92±2.73%, cytoplasm 30.37±19.47%, and Lymph Node: surface 8.94±2.43%, cytoplasm 64.9±17.62%).

The present invention has been described with reference to the preferred embodiments. It will be understood by those skilled in the art that the present invention may be embodied in various other forms without departing from the essential characteristics thereof. Therefore, the disclosed embodiments should be considered from an illustrative aspect rather than a restrictive aspect. The scope of the present invention is represented in the accompanying claims rather than the foregoing description and all of the differences within the scope of equivalents thereof should be construed as being included in the present invention.

INDUSTRIAL APPLICABILITY

As described above, the composition for preventing or treating inflammatory disease comprising the snake venom has an excellent effect for treating skin ulcers. Therefore, the composition can be effectively used by applying to pharmaceutical drugs, etc. including skin external agents for the treatment of skin ulcers, in particular for the treatment of Behcet's disease or Buerger's disease.

ADVANTAGEOUS EFFECTS

The venom of *Agkistrodon piscivorus piscivorus* or *Naja melanoleuca* according to the present invention can increase the expression of C-C chemokine receptor type 1 (CCR1) in a mouse where skin ulcer is induced and thus has an excellent effect of treating skin ulcers.

What is claimed is:

1. A method for treating a skin ulcer of a subject in need thereof, comprising administering an effective amount of a composition comprising venom of *Agkistrodon piscivorus piscivorus* or *Naja melanoleuca* to the subject.

2. The method of claim 1, wherein the composition is a pharmaceutical composition or a quasi-drug.

3. The method of claim 2, wherein the composition is in a form of a liquid, an ointment, a cream, a lotion, a spray, a patch, a gel, or an aerosol. composition which is applied to an afflicted part of skin of the subject.

4. The method of claim 1, wherein the composition is an external application composition which is applied to an afflicted part of skin of the subject.

5. The method of claim 4, wherein the afflicted part has a skin ulcer.

6. The method of claim 1, wherein the skin ulcer is induced from Behcet's disease or Buerger's disease.

* * * * *